United States Patent [19]

Huebner et al.

[11] Patent Number: 4,908,376

[45] Date of Patent: Mar. 13, 1990

[54] 2,3-DIHYDRO-2-(4,5-DIHYDROIMIDAZOL-2-YL)-INDOLES IN COMPOSITION FORM FOR REDUCING INTRAOCULAR PRESSURE

[75] Inventors: Charles F. Huebner, Chatham, N.J.; John E. Francis, Briarcliff Manor, N.Y.

[73] Assignee: Ciba-Geigy Corporation, Ardsley, N.Y.

[21] Appl. No.: 15,820

[22] Filed: Feb. 17, 1987

Related U.S. Application Data

[62] Division of Ser. No. 771,935, Sep. 3, 1985.

[51] Int. Cl.$^4$ .................................. A61K 31/415
[52] U.S. Cl. ........................................ 514/402
[58] Field of Search ................... 548/348; 514/402

[56] References Cited

U.S. PATENT DOCUMENTS 4,598,086  7/1986  Bigg et al. .................. 548/348 X

FOREIGN PATENT DOCUMENTS 0211698  2/1987  European Pat. Off. ........... 548/348

Primary Examiner—Richard A. Schwartz
Attorney, Agent, or Firm—Irving M. Fishman

[57] ABSTRACT

Compounds of the formula

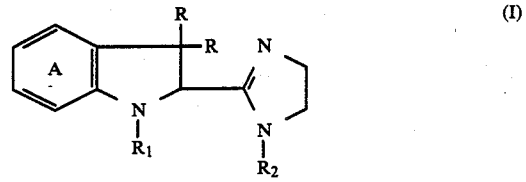

wherein each R is hydrogen or one R is hydrogen and the other is lower alkyl, $R_1$ is hydrogen, lower alkyl, aryl, aralkyl or lower carboalkoxy, $R_2$ is hydrogen or lower alkyl, and the ring A is unsubstituted or substituted by lower alkyl, lower alkoxy, halo or trifluoromethyl, and pharmaceutically acceptable salts thereof, their preparation, pharmaceutical compositions and the uses thereof, such as $\alpha_2$-adrenergic blocking agents, e.g. antidepressants, cognition enhancers and appetite suppressants, and as intraocular pressure reducing agents are disclosed.

1 Claim, No Drawings

2,3-DIHYDRO-2-(4,5-DIHYDROIMIDAZOL-2-YL)-INDOLES IN COMPOSITION FORM FOR REDUCING INTRAOCULAR PRESSURE

This is a divisional of application Ser. No. 771,935 filed on Sept. 3, 1985.

GENERAL DESCRIPTION OF THE INVENTION

The instant invention relates to novel 2,3-dihydro-2-(4,5-dihydroimidazol-2-yl)-indoles and their pharmaceutically acceptable salts having valuable pharmacological activity as $\alpha_2$-adrenergic blocking agents, and intraocular pressure reducing agents.

It is a further object of the instant invention to provide pharmacologically active compositions containing an effective amount of such novel compounds, or the pharmaceutically acceptable salts thereof, for use as $\alpha_2$-adrenergic blocking agents, and as intraocular pressure reducing agents, for example in the treatment of glaucoma.

It is yet a further object of the instant invention to provide methods of use of these novel compounds, or the pharmaceutically acceptable salts thereof, as $\alpha_2$-adrenergic blocking agents, and especially as intraocular pressure reducing agents, for example in the treatment of glaucoma.

These and other valuable objects of the instant invention are apparent from the following detailed description.

DETAILED DESCRIPTION OF THE INVENTION

It is one object of the invention to provide novel compounds of the formula

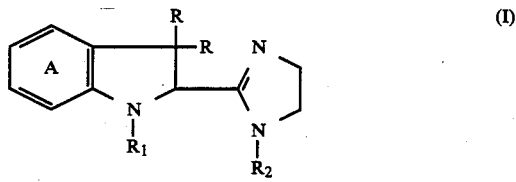

wherein
each R is hydrogen or one R is hydrogen and the other is lower alkyl;
$R_1$ is hydrogen, lower alkyl, lower carboalkoxy, phenyl which is unsubstituted or substituted by lower alkyl, lower alkoxy, halo or trifluoromethyl, or is phenyl substituted lower alkyl, wherein the phenyl ring thereof is unsubstituted or substituted by lower alkyl, lower alkoxy, halo or trifluoromethyl;
$R_2$ is hydrogen or lower alkyl;
and the ring A is unsubstituted or substituted by lower alkyl, lower alkoxy, halo or trifluoromethyl;
and the pharmaceutically acceptable acid addition salts thereof.

The term "lower" referred to above or hereinafter, defines such groups, exclusive of any carbonyl group, as having 1 to 6, preferably 1 to 4, and advantageously 1 to 2 carbon atoms. For example, lower alkyl includes methyl, ethyl, isopropyl, butyl and the like, lower alkoxy includes methoxy, ethoxy, propoxy, butoxy, and the like, and lower carboalkoxy includes carbomethoxy, carboethoxy, carbopropoxy and the like.

Halo substituents include fluoro, chloro, bromo and iodo, preferably fluoro, chloro and bromo and advantageously chloro or bromo.

The instant compounds, containing at least one asymmetric carbon atom, e.g., the carbon atom to which the dihydroimidazolyl group is attached, may be in the form of a racemate, or isolated as an optical antipode thereof. Characteristically, one of the optical antipodes will possess enhanced pharmacological activity vis-a-vis the corresponding racemate.

Also, the compounds of the invention are in the free, or basic form, or as a salt thereof. Such salts are preferably substantially non-toxic, therapeutically acceptable acid addition salts, advantageously pharmaceutically acceptable acid addition salts. However, toxic salts are also contemplated, as useful for the purification of the dihydroindole bases, for example.

Accordingly, the dihydroindole base of formula I for example, can be converted into a corresponding acid addition salt, preferably with the use of a therapeutically useful acid or anion exchange preparation, or the resulting salt can be converted into the corresponding free bases, for example, with the use of a stronger base, such as a metal or ammonium hydroxide, basic salt or cation exchange, e.g. an alkali metal hydroxide or carbonate. Said acid addition salts are of therapeutically acceptable inorganic or organic acids, such as strong inorganic acids, for example hydrohalic, e.g. hydrochloric or hydrobromic acids; sulfuric, phosphoric, nitric or perchloric acid; or of aliphatic or aromatic carboxylic or sulfonic acids, e.g. formic, acetic, propionic, succinic, glycollic, lactic, malic, tartaric, citric, ascorbic, maleic, fumaric, dihydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds of the instant invention exhibit valuable pharmacological properties, primarily as $\alpha_2$-blocking agents and as intraocular pressure reducing agents. These activities are demonstrable in animal tests advantageously using mammals, e.g. mice, rats, guinea pigs, dogs, cats or monkeys, as test objects. As $\alpha_2$-blocking agents, compounds are applied to the animal enterally or parenterally, advantageously orally, transdermally or subcutaneously, intravenously or intraperitoneally, for example within gelatin capsules or in the form of starch suspensions or aqueous solutions respectively. As intraocular pressure reducing agents, topical application to the eye in the form of an ointment or aqueous solution is preferred. The applied dosage may range between about 0.005 to 100 mg/kg/day, preferably between about 0.02 and 10 mg/kg/day, advantageously between about 0.1 and 5 mg/kg/day.

The activity of the instant compounds as $\alpha_2$-blocking agents, including cognition enhancers, and specifically as antidepressants can be shown, for example in mice by antagonism to clonidine analgesia. In this test system, the compounds of the invention are administered orally or intraperitoneally as aqueous solutions to groups of at least 10 male mice and 30 minutes thereafter 0.1 mg/kg of clonidine is intubated to them orally. After 20 minutes, they are injected with 3.75 mg/kg of phenyl-p-benzoquinone intraperitoneally and the number of mice with writhe is counted 5-15 minutes after injection. Any animal not writhing is considered a reactor, and the $ED_{50}$ for the instant compound of the present invention and clonidine combination is determined by the Berkson Logit from the number of reactors.

Because of their antidepressant activity, the compounds of the present invention are of use in the treatment or management of mental depression in patients in need of the same. Moreover, the compounds of the instant invention are likewise of use in the treatment or management of cognition impairment of the types treatable by administration of an effective amount of $\alpha_2$-blocking agents for cognition enhancement, e.g. senility, associated with aging, and in the treatment of obesity by appetite suppression.

Indicative of the antiglaucoma effect of the compounds of formula I is the intraocular pressure-lowering effect demonstrable in mammals e.g. in normotensive rabbits essentially according to the methodology described by D. E. Potter and J. M. Rowland in Experimental Eye Research 27, 615–625, 1978. The intraocular pressure-lowering effect is determined as follows:

$2 \times 50$ μl portions of a solution of the test compound in sterile water at various concentrations are applied to one eye of male, albino New Zealand rabbits weighing 3–4 kg, and $2 \times 50$ μl of the vehicle is applied to the contralateral eye serving as control. The intraocular pressure (in mm Hg) in each eye is measured tonometrically just before treatment and then at 1,2 and 3 hour intervals after administration. The difference between the intraocular pressure of the treated and control eye is determined.

One preferred embodiment of the instant invention relates to compounds of formula I wherein each R is hydrogen, $R_2$ is hydrogen, $R_1$ is phenyl or phenyl substituted by lower alkyl, lower alkoxy, halo or trifluoromethyl and the ring A's is unsubstituted or substituted by lower alkyl, lower alkoxy, halo or trifluoromethyl and pharmaceutically acceptable acid addition salts thereof. Most preferred compounds within this embodiment are those compounds wherein the ring A is unsubstitued and $R_1$ is phenyl or phenyl substituted by lower alkoxy.

An alternate preferred embodiment relates to those compounds of formula I wherein each R is hydrogen; $R_2$ is hydrogen; $R_1$ is hydrogen, lower alkyl, or lower alkyl substituted by phenyl, especially phenthyl or benzyl; and the ring A is unsubstituted or substituted by lower alkyl, lower alkoxy, halo or trifluoromethyl, and especially by methyl or methoxy; and the pharmaceutically acceptable acid addition salts thereof.

Yet another alternate preferred embodiment relates to those compounds wherein each of R is hydrogen; $R_2$ is hydrogen; $R_1$ is lower carboalkoxy and ring A is unsubstituted or is substituted by lower alkyl, lower alkoxy, halo or trifluoromethyl; and the pharmaceutically acceptable acid addition salts thereof. Especially preferred are those compounds where in the ring A is unsubstituted.

The compounds of formula 1 can be prepared by processes known per se from known compounds.

Thus, the compounds of formula I can be prepared by reacting a compound of the formula

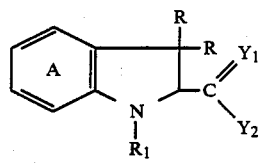

wherein A, R and $R_1$ are as defined above; $Y_1$ is =O; and $Y_2$ is hydroxy, amino, lower alkoxy, phenoxy or benzyloxy; or where $Y_1$ and $Y_2$ taken together represent =N; or a salt thereof; with an ethylene diamine of the formula $$H_2NCH_2CH_2NHR_2 \qquad (III)$$

wherein $R_2$ is as defined above; or a salt thereof, at a temperature between about 0° C. to about 135° C. optionally in the presence of an inert diluent or solvent and optionally in the presence of a condensation catalyst if desired.

Preferred $Y_2$ groups include methoxy, ethoxy, propoxy, phenoxy and benzyloxy.

Suitable diluents and solvents include benzene, toluene, methoxybenzene, cyclohexane, dioxan, tetrahydrofuran, and the like.

Suitable catalysts include trialkyl aluminum, such as trimethyl aluminum.

In the above reaction, wherein $R_1$ is hydrogen, the compound of formula II may be in protected form by converting the amino moiety of the indoline ring nitrogen to the corresponding N-acyl derivative, such as the N-lower alkanoyl derivative, which can be subsequently hydrolyzed by treating the N-acylated product of formula I with aqueous base, such as an alkali metal hydroxide solution at a temperature between about 10° C. to about 100° C.

The compounds of formula II and their N-acyl derivatives are known or can be prepared from known compounds by methods known per se.

For example, the compounds of formula II wherein the $R_1$ group has been converted to the protected N-acyl derivative can be prepared through conventional techniques, such as by reacting the corresponding compound wherein $R_1$ is hydrogen with a lower alkanoic acid anhydride, such as acetic anhydride, at a temperature between about 0° C. and 100° C., in the presence of an inert solvent or diluent if desired.

Where, in the compound of formula II, $R_1$ is hydrogen, $Y_1$ and $Y_2$ must represent =N and the amino moiety of the indoline ring nitrogen must be in protected form, e.g. in the form of the N-lower alkanoyl derivative, such as the N-acetyl derivative, in order for the desired reaction between the compounds of Formula II and III to yield the corresponding imidazoline of the formula I to be accomplished.

Those compounds of formula II wherein $Y_1$ and $Y_2$ taken together are =N can be prepared from the corresponding amide, where $Y_1$ is =O and $Y_2$ is amino, by dehydration using a conventional dehydrating agent, such as polyphosphoric acid, or a lower alkyl ester thereof, in the presence of an inert non-aqueous solvent, such as chloroform or methylene chloride, at a temperature between about 20° to about 100° C. The compounds wherein $Y_1$ is =O and $Y_2$ is amino can be prepared by reacting the corresponding acid, where $Y_1$ is =O and $Y_2$ is hydroxy, or a salt thereof, with ammonia or ammonium hydroxide in the presence of an inert solvent or diluent at a temperature between about 10° C. and about 120° C. and advantageously subsequent to conversion of the acid to a reactive derivative thereof, such as the corresponding acid halide by reaction of the acid with a halogenating agent, such as $PCl_5$, in the presence of an inert diluent or solvent, at a reaction temperature between about −10° C. to about 60° C. or by reaction of the acid with carbonyl diimidazole, or the like, at a reaction temperature between about 0° to about 80° C. Upon reaction of the resulting acid halide or carbonyl imidazole derivative with ammonia or ammonium hydroxide the corresponding amide is formed.

Those compounds of formula II in which $Y_1$ is =O and $Y_2$ is lower alkoxy, phenoxy or benzyloxy can be prepared by conventional esterification of the corresponding acid of formula II, wherein $Y_1$ is =O and $Y_2$ is hydroxy, optionally in the presence of an inert diluent, with a corresponding lower alkanol, phenol or benzyl alcohol, advantageously in the presence of an esterification catalyst, such as sulfuric acid, at a temperature between about 20° C. to about 120° C.

In the above reactions, wherein $R_1$ in the material to be converted is hydrogen, the amine group is advantageously protected by conversion to the corresponding protected form, e.g. the N-acyl derivative, such as the N-lower alkanoyl derivative, as described above. If desired or appropriate, the protecting group may be removed by treatment with aqueous base, such as an alkali metal hydroxide solution at a temperature between about 10° to about 100° C. Those compounds of formula II wherein $R_1$ is lower alkyl, lower carboalkoxy, phenyl which is substituted or unsubstituted, or phenyl substituted lower alkyl wherein the phenyl moiety is substituted or unsubstituted, are prepared from the corresponding compound of formula II wherein $R_1$ is hydrogen by conventional alkylation techniques known per se. Thus, for example the corresponding lower alkyl halide, lower alkyl haloformate, aryl halide or aralkyl halide is reacted with a compound of formula II wherein $R_1$ is hydrogen in the presence of an inert solvent, such as dimethylformamide, tetrahydrofuran, dimethylsulfoxide, optionally in the presence of a base, such as an alkali metal hydroxide or carbonate, or a tertiary amine, such as pyridine or triethylamine, and if desired in the presence of a catalyst such as cupric oxide or the like, at a temperature between about 10° C. to about 200° C.

Alternatively the corresponding indole of the formula

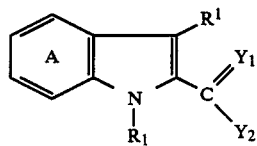
(III)

wherein A, $R_1$, $Y_1$ and $Y_2$ are as defined, and $R^1$ corresponds to R and is hydrogen or lower alkyl can be hydrogenated to the corresponding indoline of formula II by selective reduction, e.g. using an alkali borohydride or the like, such as sodium borohydride, in the presence of a diluent, such as trifluoracetic acid. In the compounds of formula III, where $R_1$ is hydrogen, the indole amine can be alkylated as set forth in the preceeding paragraph, prior to hydrogenation. Also, where $R_1$ is hydrogen, the indole amine moiety of formula III, may, if desired, be protected by N-acylation as described above in the protection of the indoline nitrogen of formula II.

The compounds of formula III may be prepared by reacting a 1-substituted hydrazine of the formula

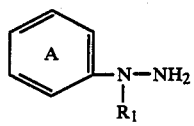
(IV)

or a salt thereof, where $R_1$ and A are as defined above, with a pyruvate derivative of the formula

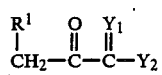
(V)

where $R^1$, $Y_1$ and $Y_2$ are as defined above, in the presence of a strong mineral acid, such as hydrochloric or hydrobromic acid, in inert solvent, such as a loweralkanol, at a temperature between about 40° to about 100° C., and recovering the resulting indole carboxylate ester of formula III.

In case mixtures of geometrical optical isomers of the above compounds, e.g. I and II, are obtained, these can be separated into the single isomers by methods in themselves known, e.g. by fractional distillation, crystallization and/or chromatography. Racemic products can likewise be resolved into the antipodes, for example, by separation of diastereomeric salts thereof, e.g. by the fractional crystallization of d- or l-tartrates, or the di-p-toluoyl-d-(or-l-)tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The pharmacologically active compounds of the invention are useful in the manufacture of pharmaceutical compositions comprising an effective amount thereof in conjunction or admixture with excipients suitable for enteral, parenteral or transdermal application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium salt and/or polyethylene glycol, for tablets also c) binders, e.g. magnesium aluminum silicate, starch paste, gelatin, tragacanth, methylcellulose, sodium carboxymethylcellulose, and/or polyvinylpyrrolidone, if if desired, (d) disintegrants, e.g. starches, agar, alginic acid or its sodium salt, enzymes of the binders or effervescent mixtures and/or e) absorbents, colorants, flavors and sweeteners. Injectable compositions and compositions for topical ocular administration are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredients.

Suitable formulations for transdermal application include an effective amount of the compound of formulas I with an excipient. Advantageous excipients include absorbable pharmacologically acceptable solvents, to assist passage through the skin of the host. Suitable, such solvents include alcohols, e.g. cyclohexanol, hexanol, glycerol and amyl alcohol; hydrocarbons such as cyclohexane, n-hexane and the like; ketones and aldehydes, including cyclohexanone and benzaldehyde; esters such as amyl acetate and benzyl propionate; etheral oils such as oil of eucalyptus, oil of rue, curin oil, limonene, thymol and 1-pinene; or halogenated hydrocarbons such as n-hexyl chloride and cyclohexyl chloride, and mixtures thereof. Characteristically, transdermal devices are in the form of a bandage comprising a backing member, a reservoir containing the compound of formula I, optionally with said excipients, optionally a rate controlling wall to meter the compound to the skin of the host at a controlled and predetermined rate over a prolonged period of time, and means to secure the device to the skin.

Suitable formulations for ocular application include, as mentioned above, aqueous solutions or suspensions. Also, the formulations may be in the form of an ointment with appropriate thickening adjuvants, such as polyvinylalcohol, polyvinylpyrrolidone, preservatives, stabilizers and the like. Alternatively, the formulation may be in the form of a conventional controlled release device, such as a loaded hydrogel or the like, for placement in the conjunctional sac of the eye, to continuously release the compound of formula I into the ocular environment.

The following examples are intended to illustrate the invention and are not to be construed as being limitations thereon. Temperatures are given in degrees Centigrade, and all parts wherever given are parts by weight unless otherwise specified. If not mentioned otherwise, all evaporations are performed under reduced pressure, preferably between about 15 and 100 mmHg.

EXAMPLE 1

2,3-Dihydro-2-(4,5-dihydro-1H-imidazol-2-yl)-1H-indole

Four grams of 2-cyano-N-acetyl indoline and 5.6 g of ethylenediamine tosylate are intimately mixed and heated as a melt at 120° for two hrs. After cooling, 10 ml of water are added to effect solution followed by 10.0 ml of 3N sodium hydroxide and the mixture is extracted 2 times with 50 ml of ethyl acetate. The ethyl acetate is extracted with 10 ml of 3N hydrochloric acid and the acid extract cooled and basified with concentrated ammonium hydroxide. The desired crystalline imidazoline is filtered and recrystallized from isopropanol.

The starting material is prepared as follows: To a stirred suspension of 12.0 g of N-acetyl indoline-2-carboxylic acid in 100 ml of tetrahydrofuran are added 11.5 g of carbonyl diimidazole. After 30 min., 15 ml of concentrated ammonium hydroxide are added. The crystalline amide is filtered, m.p. 245°–250°.

A mixture of 3.7 g of the above, thoroughly dried amide and 18 g of polyphosphoric ethyl ester in 18 ml of chloroform, is stirred and refluxed for one hr. The solvent is removed in vacuo, 20 g of ice added and, with stirring, excess sodium carbonate added to destroy excess polyphosphoric ester. The mixture is extracted with methylene chloride, the extract evaporated to dryness in vacuo and the crystalline residue recrystallized from ethyl acetate, m.p. 98°–101°. This nitrile is used as described above.

EXAMPLE 2

2,3-Dihydro-2-(4,5-dihydro-1H-imidazol-2-yl)-1-carboethoxy indole hydrochloride

A mixture of 2.0 g of 2,3-dihydro-2-cyano-1-carboethoxyindoline and 2.2 g of ethylenediamine tosylate is reacted as described in Example 1. The workup proceeds analogously. The base melts 135°–137° and the hydrochloride prepared by adding 4N ethanolic hydrochloric acid to a solution of the base in the minimum of hot isopropanol, melts 225°–230° (dec).

The requisite nitrile is prepared as follows: To a stirred solution of 10.0 g of indoline-2-carboxylic acid and 20.0 ml of triethylamine i 100 ml of acetone are added with cooling 7.0 ml of ethyl chloroformate. After 2 hrs., the solution is evaporated to dryness. The residue is taken up in a small amount of water, acidified with concentrated hydrochloric acid and extracted with methylene chloride. The resulting carboxylic acid is converted, as described in Example 1 to the amide. The amide is then dehydrated to the nitrile as described in Example 1. The non-crystalline nitrile is used as described above.

EXAMPLE 3

2,3-Dihydro-2-(4,5-dihydro-1H-imidazol-2-yl)-1-methylindole fumarate

Freshly distilled ethylene diamine (1.2 ml) is added dropwise under nitrogen to a solution of 2M trimethyl aluminum in toluene (8.2 ml), maintaining the temperature at 10° C. The solution is allowed to rise to room temperature and stirred at this temperature for 1 hr.

A solution of methyl-2,3-dihydro-1-methylindolecarboxylate (1.8 g) in toluene (10 ml) is added dropwise. Temperature rises to 50° C. and then subsides. The mixture is stirred at reflux for 3 hrs., cooled in an ice bath and quenched with water (4.3 ml), methanol (13.7 ml), and methylene chloride (13.7 ml). The mixture is stirred at reflux for 15 mins. and filtered hot through a bed of anhydrous sodium sulfate, washing with methylene chloride. The filtrate is evaporated to dryness. Ethyl acetate (50 ml) is added to the residue and heated at reflux for 15 mins, filtered hot through a bed of anhydrous sodium sulfate and evaporated to dryness to obtain the solid base, m.p.=97°–100° C.

This is dissolved in ethanol and a solution of an equivalent weight of fumaric acid in ethanol is added. The mixture is cooled and filtered to obtain the desired solid, m.p.=182°–183° C.

The requisite starting material is made as follows:

A solution of methyl-1-methylindole-carboxylate* (6.0 g) in trifluoroacetic acid (50 ml) is cooled in an ice bath as sodium borohydride pellets (6.0 g) are added slowly, keeping the temperature below 10° C. The slurry is allowed to rise to room temperature and then stirred overnight. The unreacted sodium borohydride is decomposed with 50% sodium hydroxide and the mixture is extracted several times with ether. The extracts are washed with saturated sodium chloride solution, dried over sodium sulfate, and evaporated to dryness to obtain an orange oil. This is distilled in a kuegelrohr (b.p.=128–150/0.2 mm) to yield colorless liquid, methyl-2, 3-dihydro-1-methylindole-carboxylate.

*Org. Prep. & Proc. Int. 4, 51–53 (1972).

EXAMPLE 4

2,3-Dihydro-2-(4,5-dihydro-1H-imidazol-yl)-1-benzylindole fumarate

The free base of ethyl-1-benzyl-2,3-dihydroindole carboxylate obtained from the hydrochloride salt was reacted with ethylene diamine and trimethylaluminum as in the above example 3 to obtain solid base, m.p.=134°–138° C. To an alcoholic solution of this is added an alcoholic solution of fumaric acid (1 equivalent) to obtain the fumarate salt, m.p. 168°–170° C.

The requisite starting material was prepared as follows: 1-Benzylphenylhydrazine hydrochloride* (140 g), ethyl pyruvate (69 ml), and 10% concentrated hydrochloric acid in ethanol (1500 ml) are heated together for 5 hours at 72°–77° C. The mixture is cooled, diluted with water and extracted with ether. The organic layer is washed with saturated sodium chloride, dried over sodium sulfate, and evaporated to dryness to obtain a viscous oil which crystallized. This is cooled in an ice bath suspended in hexane to obtain ethyl-1-benzylindole-carboxylate, m.p. 55°–56° C.

*Bah. Inst. Quinn. Univ. Nac. auton., Mex. 18, (1966)

Ethyl-1-benzylindole carboxylate is reduced as in the above example 3. The obtained oil is dissolved in ether and ethanolic hydrogen chloride is added to yield ethyl-1-benzyl-2,3-dihydroindole-carboxylate hydrochloride, m.p. 123°–124° C.

EXAMPLE 5

2,3-Dihydro-2-(4,5dihydroimidazol-2-yl)-1-phenylindole 2,3-Dihydro

To a stirring solution of 2 molar trimethylaluminum in toluene (13.1 ml) at 10° C. under argon is added ethylenediamine (1.75 ml) dropwise under cooling to maintain a temperature of +10° C. It is allowed to ware to room temperature and then ethyl-2,3-dihydro-1-phenylindole-2-carboxylate (3.5 g) in toluene (15 ml) is added under argon. The whole is heated gradually to reflux and maintained at this temperature under argon for 18 hours. This cooled mixture is quenched in water (40 ml) and treated with methanol (40 ml) and methylene chloride (40 ml). The aqueous layer is separated and extracted further with methylene chloride (3×100 ml). The combined organic extracts are dried over sodium sulfate and concentrated to dryness at reduced pressure. The residue is dissolved in boiling ethyl acetate (150 ml), filtered through sodiumsulfate and concentrated to reduced pressure to a small volume from which yellow solid precipitates. The pure dl-2,3-dihydro-2-(4,5-dihydroimidazol-2-yl)-1-phenylindole, mp. 141°–144°, is thus obtained.

The starting indoline ester is prepared as follows: To a solution of ethyl 1-phenylindole-2-carboxylate [10 g] prepared as described by Dolby and Lord, J. Org. Chem. 34. (10) 2988–2993)] in trifluoroacetic acid (80 ml) is added under mechanical stirring and with ice cooling sodium borohydride (7.1 g) little by little to maintain a temperature of 0°–10° C. It is stirred under nitrogen at 10° for 7 hrs., neutralized with cold 10N sodium hydroxide, extracted with ether (2×150 ml) and the ether solution dried over magnesium sulfate and concentrated to dryness at reduced pressure to obtain the corresponding indoline ethyl ester.

EXAMPLE 6

2,3-Dihydro-2-(4,5-dihydroimidazol-2-yl)-1-(3-methoxyphenyl) indole

By the process of Example 5, ethyl-2,3-dihydro-1(3-methoxyphenyl)indole-2-carboxylate is converted to dl-2,3-dihydro-2-(4,5-dihydroimidazol-2-yl)-1-(3-methoxyphenyl)indole, mp. 123°–125°.

The starting ester is prepared in the following manner: A mixture of indole-2-carboxylic acid (8.06 g), m-bromoanisole (9.35 g), anhydrous potassium carbonate (7 g) and cupric oxide (0.25 g) in dimethylformamide (10 ml) is heated at 170° C. under nitrogen for 18 hrs., diluted with a further 20 ml of solvent and heated 6 hours longer. It is cooled, diluted with water (500 ml) and extracted with methylene chloride (3×100 ml). The filtered aqueous layer is acidified with cold concentrated hydrochloric acid, refrigerated overnight and the precipitated product recrystallized from methanol to afford pure 1-(3-methoxypheny)indole-2-carboxylic acid (6.1 g), mp. 194°–196°. This acid (3.3 g) absolute ethanol (100 ml) and concentrated sulphuric acid (1.1 ml) are refluxed overnight, cooled, treated with water (50 ml) and the ethyl ester crystallizes. The crude ester (34 g) in trifluoroacetic acid (280 ml) is reduced with sodium borohydride (17.3 g) as described in Example 5 to afford ethyl 2,3-dihydro-1-(3-methoxyphenyl)indole-2-carboxylate as an oil.

What is claimed is:

1. A pharmaceutical composition comprising a pharmaceutically acceptable excipient and an effective intraocular pressure reducing amount of a compound of the formula

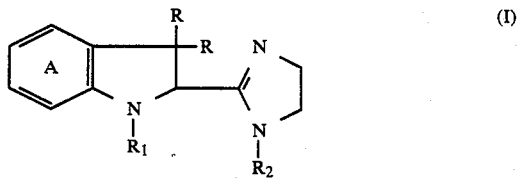

wherein each R is hydrogen or one is hydrogen and one is lower alkyl; $R_2$ is hydrogen or lower alkyl; and ring A is unsubstituted or substituted by lower alkoxy, and $R_1$ is hydrogen, methyl, or benzyl; or a pharmaceutically acceptable acid addition salt thereof.

* * * * *